(12) United States Patent
Francis et al.

(10) Patent No.: US 10,286,539 B2
(45) Date of Patent: May 14, 2019

(54) DUAL AXIS HOOK ASSEMBLY FOR A POWER TOOL

(71) Applicants: Robert Bosch Tool Corporation, Broadview, IL (US); Robert Bosch GmbH, Stuttgart (DE)

(72) Inventors: Noel Francis, Skokie, IL (US); Brady Groth, Chicago, IL (US); Marco Laubach, Wheeling, IL (US)

(73) Assignees: Robert Bosch Tool Corporation, Broadview, IL (US); Robert Bosch GmbH, Stuttgart (DE)

( * ) Notice: Subject to any disclaimer, the term of this patent is extended or adjusted under 35 U.S.C. 154(b) by 67 days.

(21) Appl. No.: 15/284,564

(22) Filed: Oct. 4, 2016

(65) Prior Publication Data
US 2017/0021490 A1   Jan. 26, 2017

Related U.S. Application Data

(63) Continuation of application No. 14/452,664, filed on Aug. 6, 2014, now Pat. No. 9,457,461.

(Continued)

(51) Int. Cl.
*B23D 45/16* (2006.01)
*B27B 3/12* (2006.01)
(Continued)

(52) U.S. Cl.
CPC ............... *B25F 5/02* (2013.01); *A61K 47/32* (2013.01); *A61K 47/58* (2017.08); *B23D 45/16* (2013.01);
(Continued)

(58) Field of Classification Search
CPC .... C08F 220/36; C08F 220/18; C08F 220/00; C08F 220/34; A61K 47/32; A61K 47/58;
(Continued)

(56) References Cited

U.S. PATENT DOCUMENTS 1,806,528 A   5/1931   Fegley et al.
2,737,985 A   3/1956   Utz
(Continued)

FOREIGN PATENT DOCUMENTS

DE    10358573 A1    7/2005

OTHER PUBLICATIONS

International Search Report and Written Opinion corresponding to PCT Application No. PCT/US2014/049893, dated Nov. 18, 2014 (15 pages).
(Continued)

*Primary Examiner* — Ghassem Alie
*Assistant Examiner* — Bharat C Patel
(74) *Attorney, Agent, or Firm* — Maginot Moore & Beck LLP

(57) ABSTRACT

A power tool includes a housing and a hook assembly. The hook assembly includes a hook support and a hook member. The hook support is rotatably attached to the housing for rotation about a first axis. The hook member has a shank portion and a hook portion. The shank portion defines a second axis that is transverse to the first axis and is configured to rotate with respect to the hook support about the second axis.

8 Claims, 8 Drawing Sheets

Related U.S. Application Data

(60) Provisional application No. 61/682,820, filed on Aug. 6, 2013.

(51) Int. Cl.

| | | |
|---|---|---|
| *B27B 3/26* | (2006.01) | |
| *B23D 45/00* | (2006.01) | |
| *B27B 23/00* | (2006.01) | |
| *B27B 21/00* | (2006.01) | |
| *B26B 19/02* | (2006.01) | |
| *B25F 5/02* | (2006.01) | |
| *A61K 47/32* | (2006.01) | |
| *C08F 220/00* | (2006.01) | |
| *C08F 220/36* | (2006.01) | |
| *C08F 220/34* | (2006.01) | |
| *B23Q 13/00* | (2006.01) | |
| *B27B 5/29* | (2006.01) | |
| *B27B 9/00* | (2006.01) | |
| *A61K 47/58* | (2017.01) | |

(52) U.S. Cl.
  CPC ............... *B23Q 13/00* (2013.01); *B27B 5/29* (2013.01); *B27B 9/00* (2013.01); *C08F 220/00* (2013.01); *C08F 220/34* (2013.01); *C08F 220/36* (2013.01)

(58) Field of Classification Search
  CPC ........... B23D 45/16; B23Q 13/00; B25F 5/02; B27B 5/29; B27B 9/00
  USPC ...... 30/388, 392, 166.3, 514, 517–519, 210, 30/216, 276
  See application file for complete search history.

(56) References Cited

U.S. PATENT DOCUMENTS

| | | | |
|---|---|---|---|
| 3,317,174 A | | 5/1967 | Wilkerson, Jr. |
| 3,805,639 A | | 4/1974 | Peter |
| 3,886,658 A | | 6/1975 | Wikoff |
| 4,406,064 A | * | 9/1983 | Goss .................. B27B 9/00 30/298.4 |
| 4,787,145 A | * | 11/1988 | Klicker ................ B27B 9/00 248/291.1 |
| 4,895,336 A | | 1/1990 | Lieberman |
| 5,265,312 A | | 11/1993 | Okumura |
| 5,743,451 A | | 4/1998 | Kahn |
| 5,850,698 A | * | 12/1998 | Hurn .................. B23D 47/126 30/275.4 |
| 5,924,667 A | * | 7/1999 | Grahn .................. F21L 15/14 248/304 |
| 6,056,668 A | | 5/2000 | Nagashima |
| 6,321,622 B1 | | 11/2001 | Tsuge et al. |
| 6,502,949 B1 | | 1/2003 | Horiyama et al. |
| 6,679,406 B2 | | 1/2004 | Sakai et al. |
| 6,722,046 B2 | | 4/2004 | Evenson |
| 6,892,459 B2 | | 5/2005 | Okumura et al. |
| 7,111,364 B2 | * | 9/2006 | Bader .................. B25F 5/02 16/110.1 |
| 7,455,001 B1 | * | 11/2008 | Waters .................. B25H 3/00 16/406 |
| 7,681,661 B2 | | 3/2010 | Sakai et al. |
| 8,308,034 B2 | | 11/2012 | Shibata et al. |
| 8,443,913 B2 | | 5/2013 | Nagasaka et al. |
| 8,534,375 B2 | | 9/2013 | Matsumoto et al. |
| 8,573,322 B2 | | 11/2013 | Nagasaka et al. |
| 8,833,485 B2 | | 9/2014 | Svennung et al. |
| 2002/0122707 A1 | | 9/2002 | Sakai et al. |
| 2004/0035274 A1 | | 2/2004 | Fasnacht et al. |
| 2004/0050888 A1 | * | 3/2004 | Warner .................. A45F 5/00 224/269 |
| 2004/0148786 A1 | * | 8/2004 | Achterberg ............ B23D 53/12 30/298.4 |
| 2005/0200087 A1 | | 9/2005 | Vasudeva et al. |
| 2006/0070761 A1 | * | 4/2006 | Vahabi-Nejad ........... B25C 7/00 173/217 |
| 2006/0117580 A1 | | 6/2006 | Serdynski et al. |
| 2008/0000939 A1 | | 1/2008 | Walsh |
| 2008/0148915 A1 | | 6/2008 | Nickels et al. |
| 2008/0185410 A1 | * | 8/2008 | Oomori .................. B25C 7/00 224/269 |
| 2009/0134191 A1 | * | 5/2009 | Phillips .................. A45F 5/02 224/269 |
| 2011/0289786 A1 | | 12/2011 | Bijsterveldt et al. |
| 2012/0292472 A1 | | 11/2012 | Segura et al. |
| 2013/0062498 A1 | * | 3/2013 | Ito .................. B25B 21/00 248/672 |

OTHER PUBLICATIONS

Supplementary Partial European Search Report corresponding to European Patent Application No. 14 83 5232 (11 pages).

* cited by examiner

DUAL AXIS HOOK ASSEMBLY FOR A POWER TOOL

CROSS-REFERENCE TO RELATED APPLICATIONS

This application claims priority to U.S. Provisional Application Ser. No. 61/862,820 entitled "DUAL AXIS HOOK ASSEMBLY FOR A POWER TOOL" by Francis et al., filed Aug. 6, 2013, and to U.S. patent application Ser. No. 14/452,664 entitled "DUAL AXIS HOOK ASSEMBLY FOR A POWER TOOL" by Francis et al., filed Aug. 6, 2014, the disclosures of which are hereby incorporated by reference herein in their entirety.

TECHNICAL FIELD

The disclosure is relates generally to accessories for power tools, and, in particular, to hooks and hanging elements for suspending power tools.

BACKGROUND

Suspension accessories, such as hooks, have been incorporated into various power tools to enable the power tool to be suspended on another hook, ledge, rod, or other similar type of object provided on a wall, bench, or belt of an operator. Such a suspension accessory provides a convenient way to stow a tool, temporarily or otherwise, when not in use. However, a suspension accessory, such as a hook, must necessarily extend outwardly from the tool to be of use. As a result, a hook or similar type of structure can inadvertently come into contact with other objects and interfere with the use of the tool.

DETAILED DESCRIPTION

Figure 1:
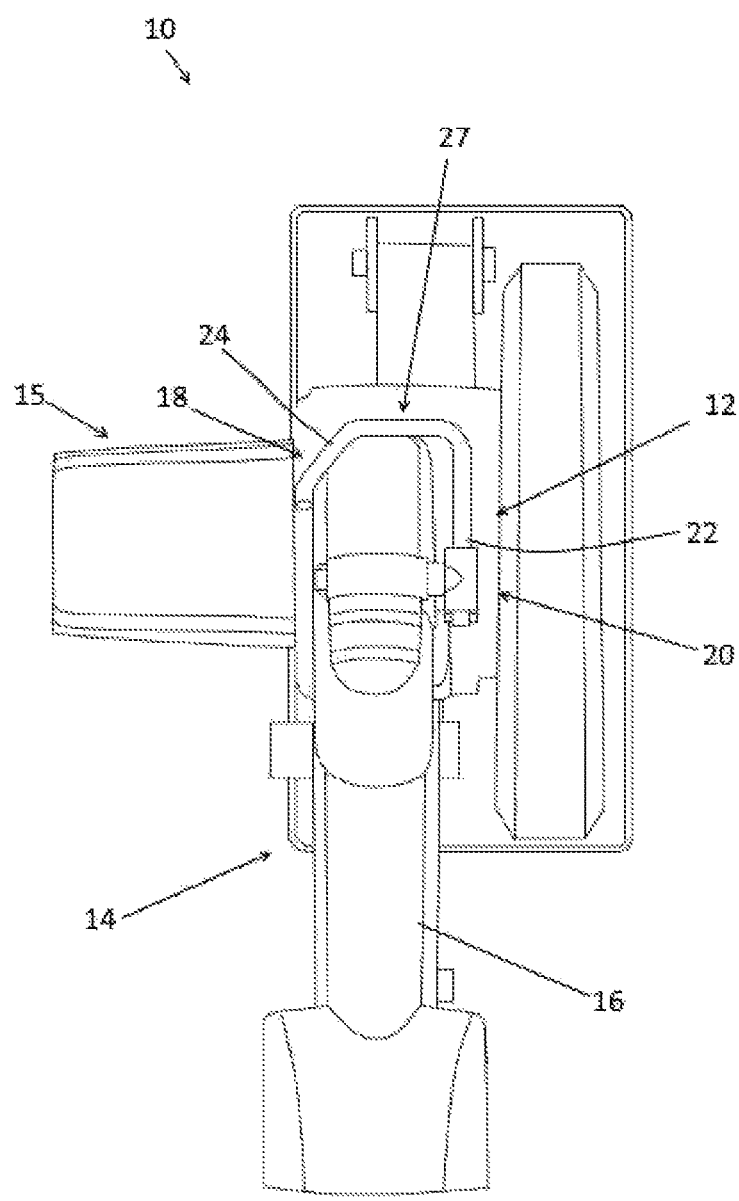
FIG. 1 is a top plan view of an one embodiment of a power tool equipped with a dual axis hook assembly in accordance with the disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one of ordinary skill in the art to which this disclosure pertains.

The present disclosure is directed to a dual axis hook assembly for use with power tools. The hook assembly can be incorporated into the housing of the power tool to enable the tool to be suspended from a hook or rod when not in use. The hook assembly has a dual axis design that enables the hook element to be positioned close or adjacent to the body of the tool to minimize possible interference with use of the tool. When the tool is not being used, the hook element can be extended outwardly from the body of the tool and oriented in a plurality of directions to facilitate the hanging the tool.

One embodiment of a power tool 10 equipped with a dual axis hook assembly 12 in accordance with the disclosure is depicted in FIGS. 1-8. In the embodiments disclosed herein, the power tool 10 comprises a handheld circular saw. In alternative embodiments, a dual axis hook assembly, such as disclosed herein, may be incorporated into any type of power tool, hand tool, tool accessory, cordless tool, corded tool, specialty tool, and substantially any object that could benefit from having the hook assembly of the disclosure.

Referring to FIG. 1, the power tool 10 includes a housing 14 having a motor portion 15 and a handle portion 16. The motor portion 15 encloses the internal components of the tool, such as a motor, a gear, and drive system (not shown). The handle 16 extends from the motor portion 15 and provides an operator a place to grip and hold the tool during use. The dual axis hook assembly 12 is incorporated a suitable location of the housing 14. The location used for the hook assembly depends on the type of tool, the weight distribution of the tool, the location of the handle, and other factors. In the embodiment of FIGS. 1-8, the hook assembly 12 is located on an upper portion of the housing 14 near the handle 16. Although one hook assembly is illustrated, two or more hook assemblies can be incorporated to the power tool without departing from the spirit of the disclosure.

The hook assembly includes a hook 18 and a support 20. The hook 18 has a shank portion 22 and a hook portion 24. The shank portion 22 comprises a straight, longitudinal section that is used to attach the hook 18 to the support 20 on the tool housing 14 and that defines one axis A of rotation for the hook assembly 12. The hook portion 24 extends in a radial direction from one end of the shank 22 and has suitable hook shape for use in suspending the tool.

Figure 4A:
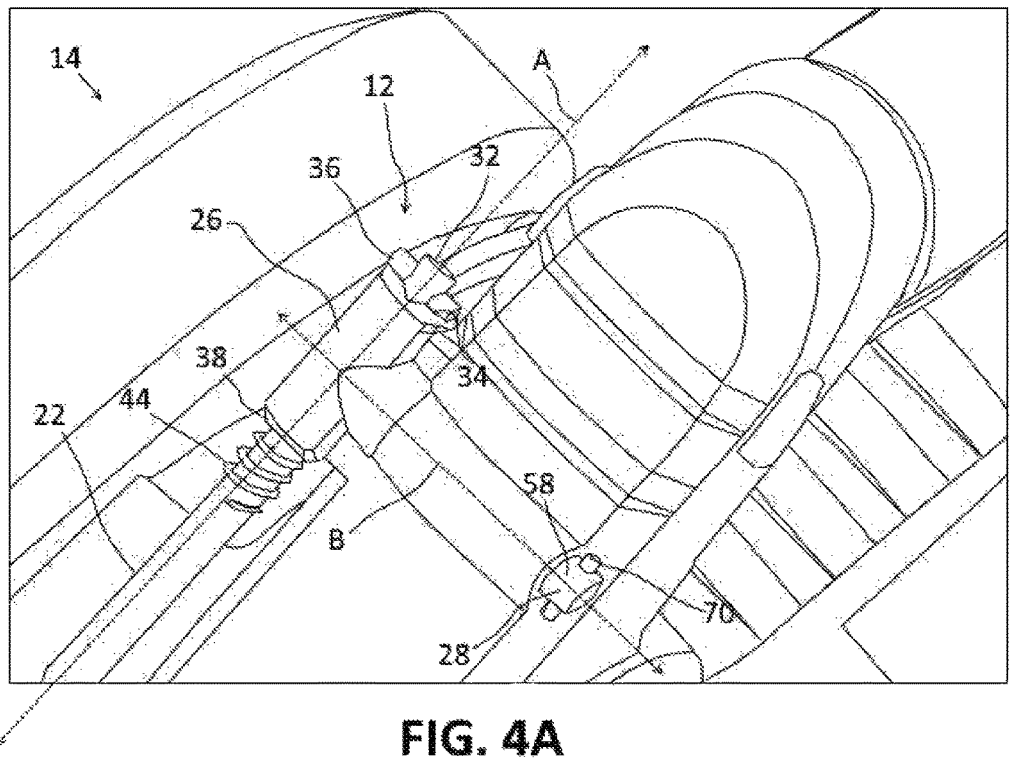
FIG. 4A is a perspective view of the power tool of FIG. 1 showing the hook assembly in greater detail.
Figure 4B:
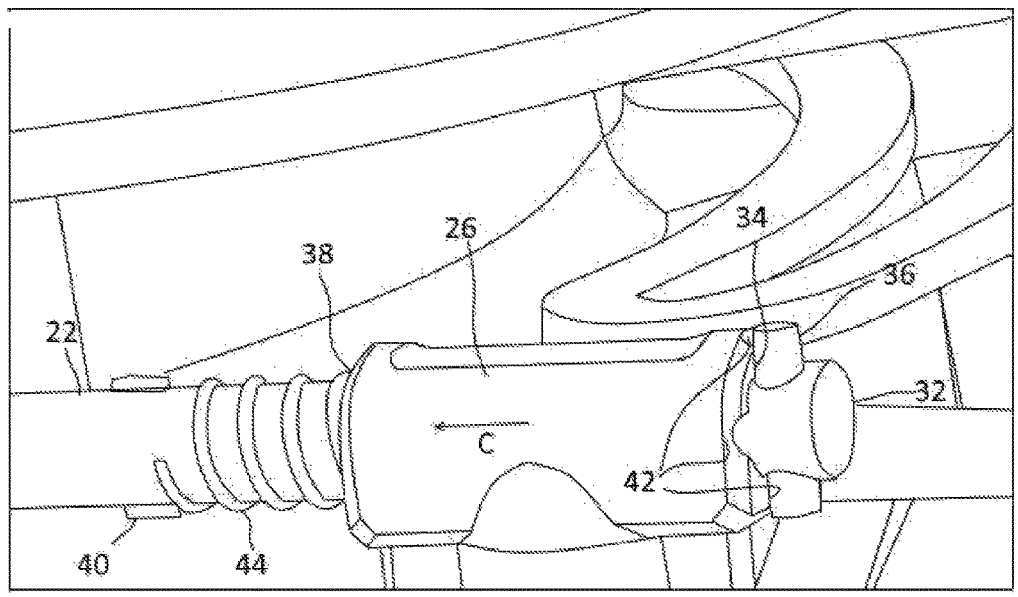
FIG. 4B is a perspective view of the power tool of FIG. 1 showing the hook retaining portion of the hook assembly of FIG. 4A in greater detail.
Figure 5:
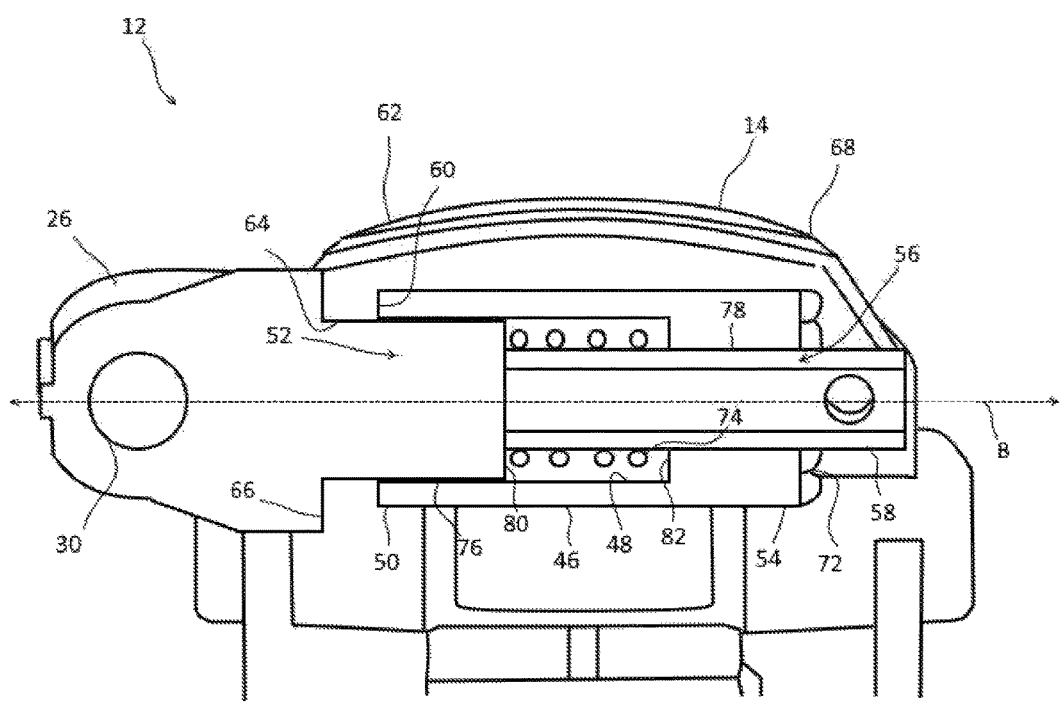
FIG. 5 is cross-sectional view of a portion of the power tool of FIG. 1 in including the hook assembly.

Referring to FIGS. 3-5, the support 20 includes a hook retaining portion 26 and a shaft portion 28. The hook retaining portion 26 is located exterior to the housing 14 and defines an open-ended passage 30 in which the shank portion 22 of the hook member 18 is rotatably received. The shaft portion 28 of the support 20 is used to secure the hook assembly 12 to the housing 14 of the power tool. In addition, the shaft portion 28 is rotatably supported within a portion of the housing 14 so as to define the second axis of rotation B for the hook assembly 12.

The passage 30 is sized and shaped complementary to the shank portion 22 of the hook 18 and is configured to allow rotational and axial movement of the shank portion 22 within the passage 30. Referring to FIGS. 3 and 4, the end 32 of the shank portion 22 protrudes from the opening 34 at one end of the passage 30, and a fastener structure 36 is extended through the protruding end 32 to prevent the withdrawal of the shank portion 22 from the passage 30. The portion of the shank 22 extending from the opening 38 at the other end of the passage 30 is provided with a collar structure 40 to limit the advancement of the shank 22 into the passage. In alternative embodiments, the shank 22 of the hook member 18 may be rotatably and translatably retained in the passage 30 of the hook retaining portion 26 in any suitable manner.

The hook retaining portion 26 may be configured to releasably retain the shank 22 at a plurality of discrete angular positions in relation to the retaining portion 26 and the passage 30. This configuration provides flexibility in orienting the hook member 18 to suspend the tool at a preferred position and/or orientation and to maintain the tool in this position while suspended. In one embodiment, the discrete angular positions for the hook member 18 are enabled using detents.

Referring to FIG. 4B, in one embodiment, the hook retaining portion 26 includes detent structures 42 that are arrayed about the opening 34 to the passage from which the end 32 of the shank 22 extends. The detent structures 42 are configured to cooperate with the fastener structure 36 to releasably retain the shank 22 at a plurality of discrete angular positions in relation to the hook retaining portion 26. In this embodiment, the fastener structure 36 comprises a rod or pin, such as a roll pin, that protrudes outwardly from one or both sides of the shank end 32. The detent structures 42 comprise notches or grooves for receiving the protruding portions of the pin 36.

A biasing member 44, such as a compression spring, machined spring, a spring with shape forming alloy or material, is used to bias the protruding portions pin 36 into the notches 42. The spring 44 is positioned around the shank 22, between the collar structure 40 and the hook retaining portion 26, to bias the shank 22 in the direction C (FIG. 4B). To rotate the hook member 18 from one angular position to another, the shank 22 of the hook member 18 is pushed and/or rotated with sufficient force to overcome the biasing force of the spring 44 so that the protruding portions of the pin 36 can be rotated out of one set of notches 42 and into another set of notches 42. The collar structure 40 is spaced apart from the hook retaining portion 26 to provide adequate clearance for the spring 44 to be compressed so the shank 22 can be rotated.

Figure 6A:
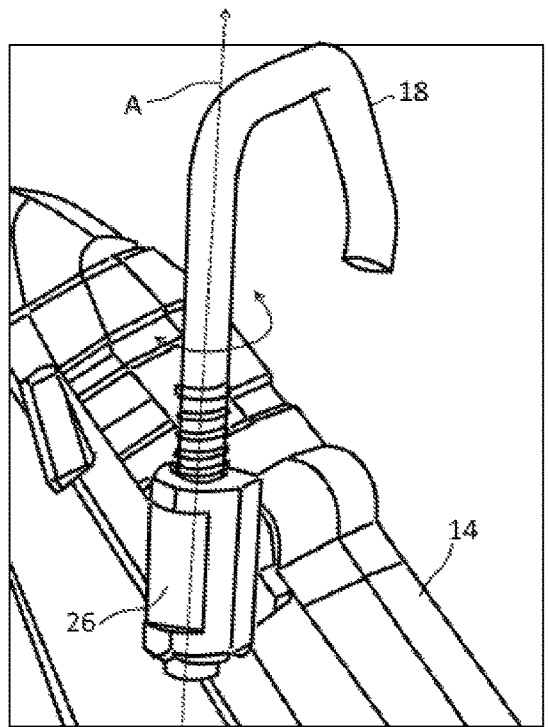
FIG. 6A depicts the hook assembly of FIG. 1 in an extended position with the hook oriented in a first radial direction.
Figure 6B:
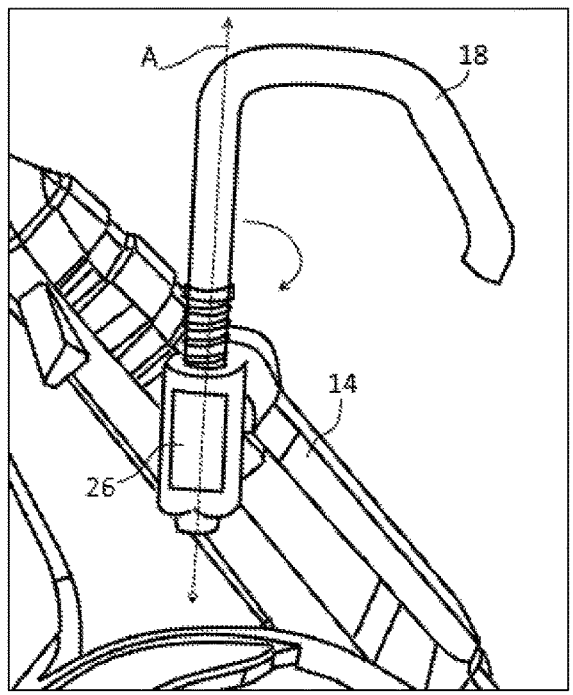
FIG. 6B depicts the hook assembly of FIG. 1 in an extended position with the hook oriented in a second radial direction.

The number of notches 42 used and the positioning of the notches 42 about the opening 34 to the passage 30 control the number of discrete angular positions for the hook member 18 about the axis A. In FIG. 4B, four evenly spaced grooves are provided around the opening 34 to the passage 30 which enable the hook member to be retained at 90° increments about the axis A. Two of these positions are depicted in FIGS. 6A and 6B, respectively. In alternative embodiments, more or fewer grooves may be used to provide a greater or lesser number of possible orientations for the hook member 18.

Figure 2:
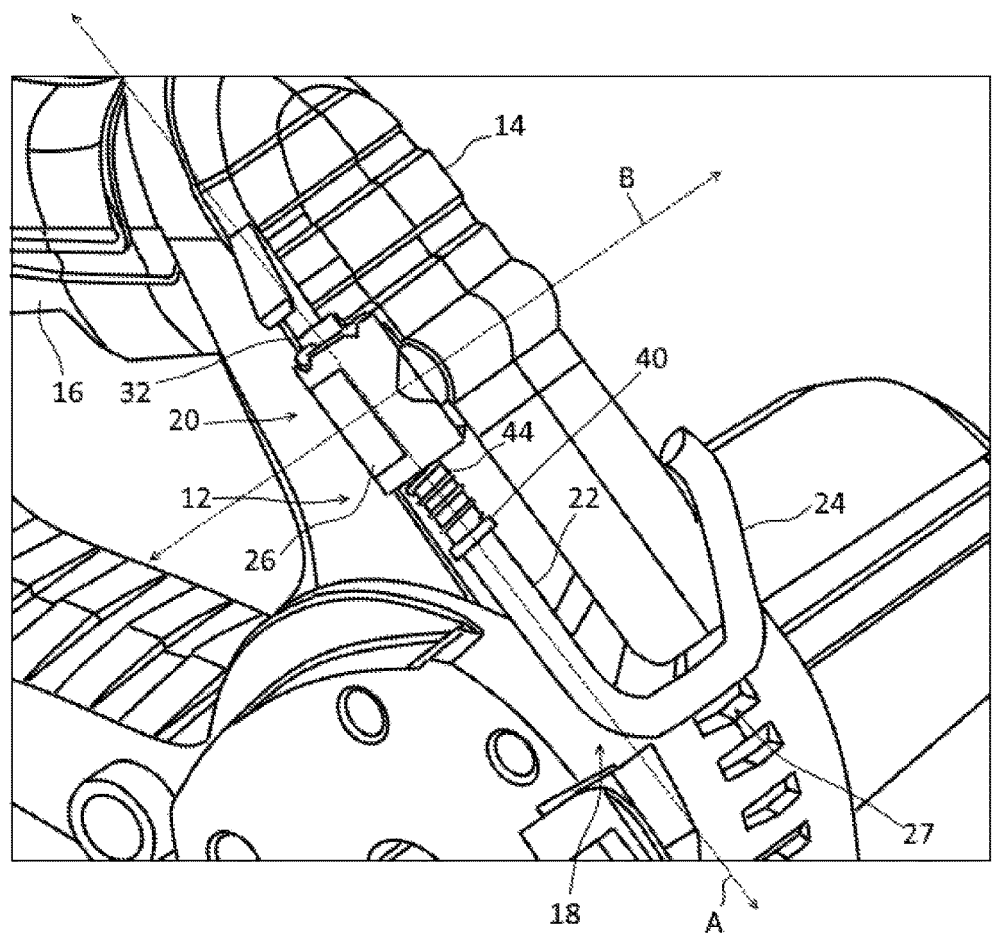
FIG. 2 is a fragmentary perspective view of the power tool of FIG. 1.
Figure 3A:
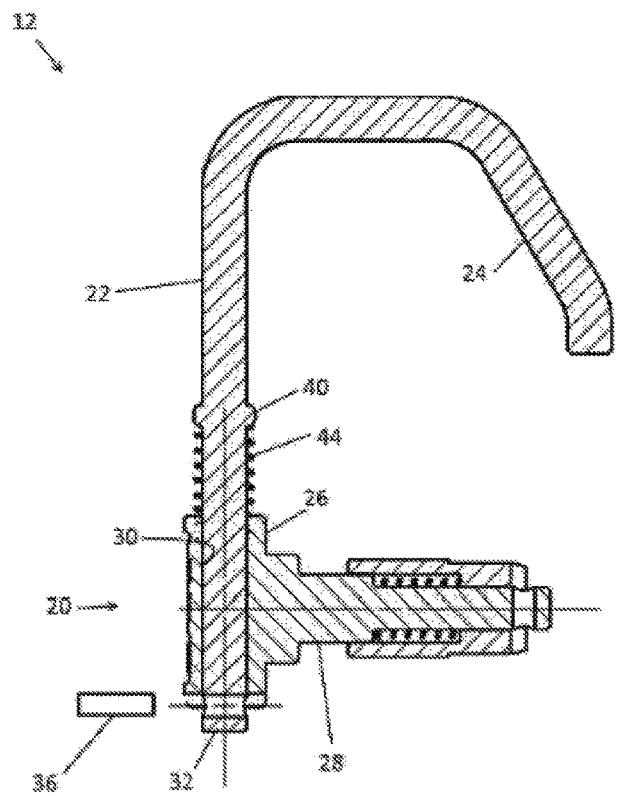
FIGS. 3A and 3B are plan views of the dual axis hook assembly shown removed from the power tool.
Figure 3B:
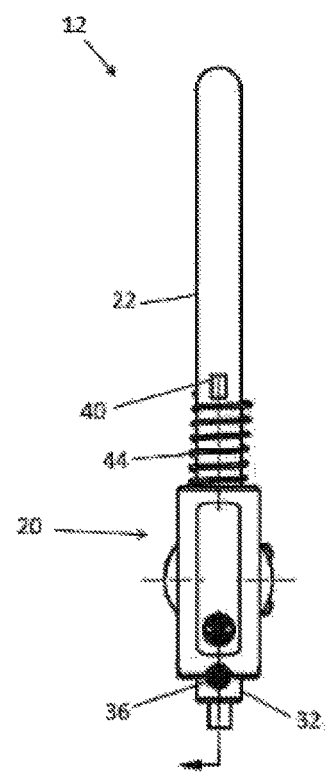
Figure 7A:
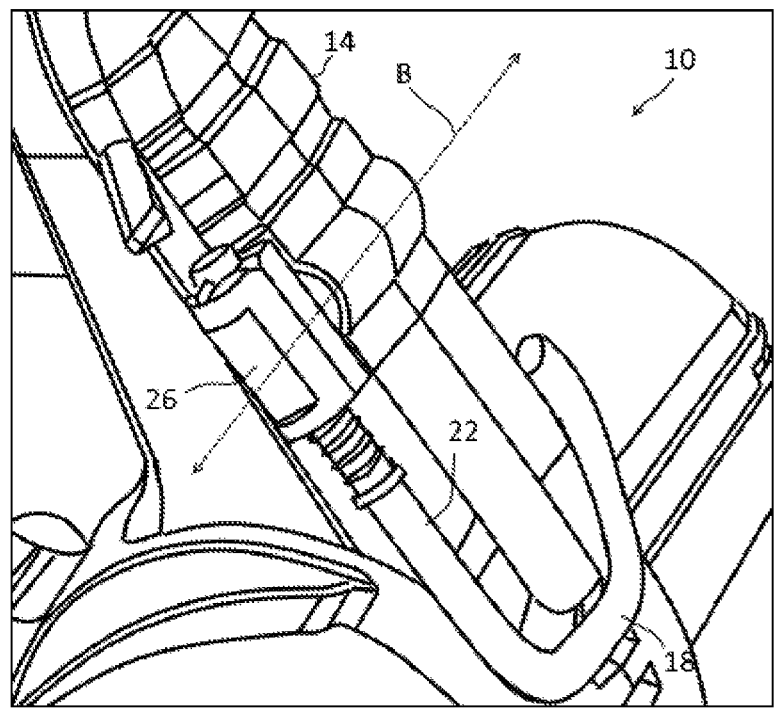
FIG. 7A depicts the hook assembly of FIG. 1 in a stowed position relative to the tool housing.
Figure 7B:
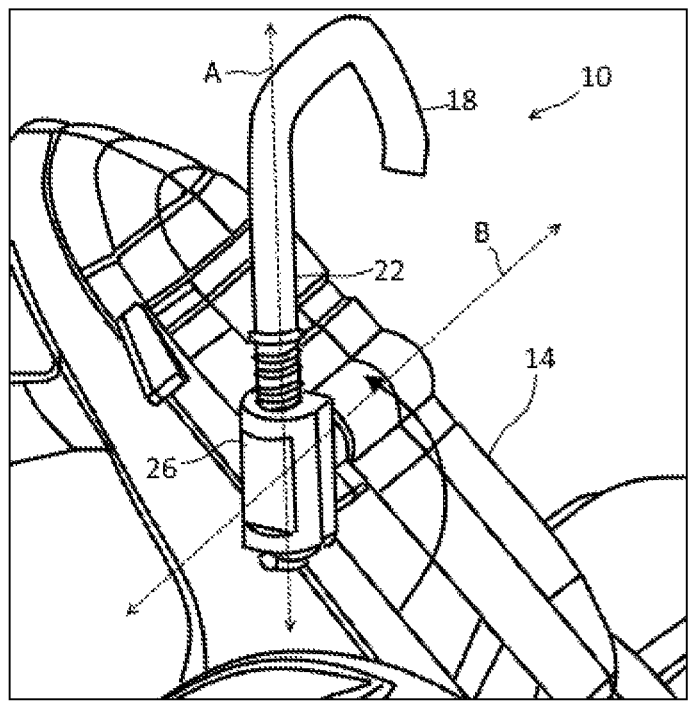
FIG. 7B depicts the hook assembly of FIG. 1 in an extended position relative to the tool housing.
Figure 8A:
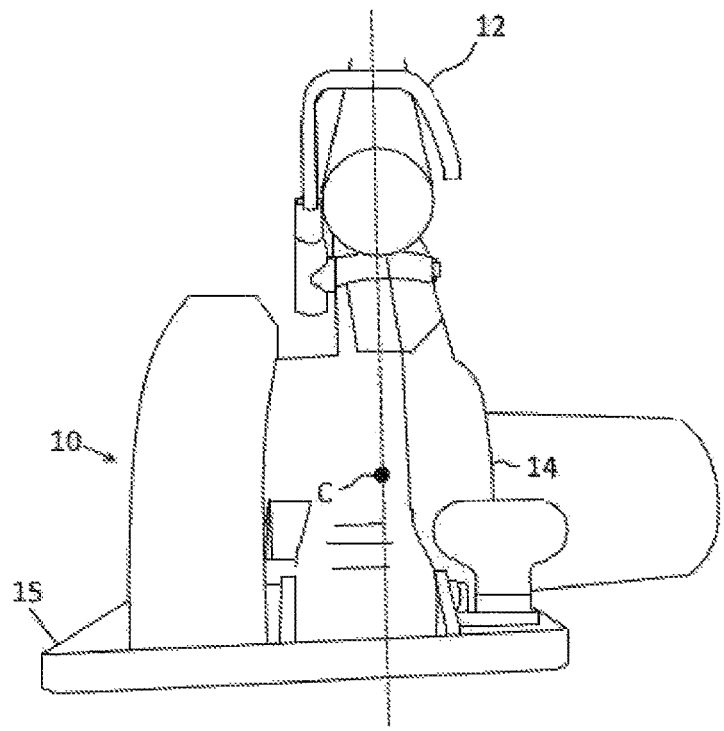
FIG. 8A is a front view of a power tool suspended by the dual axis hook assembly.
Figure 8B:
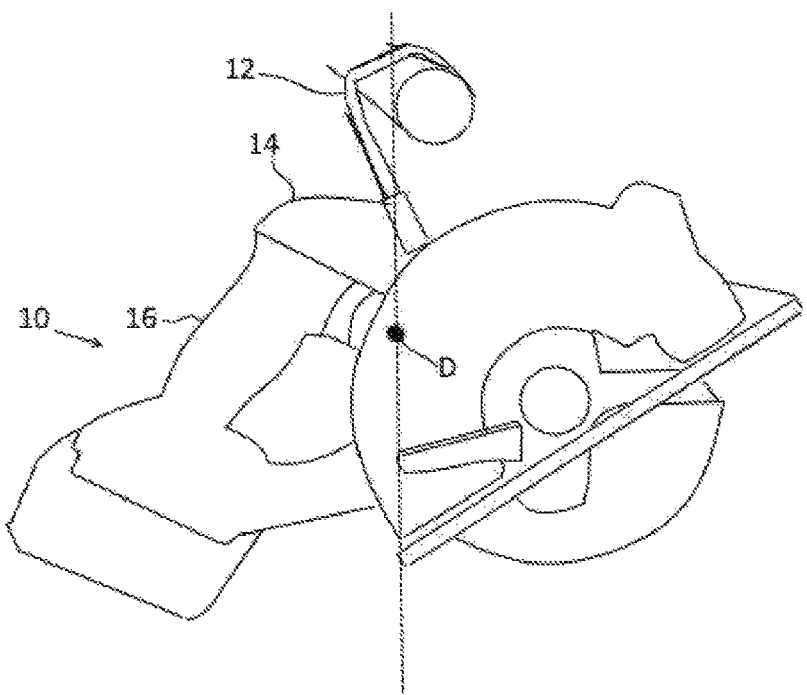
FIG. 8B is a side view of the power tool of FIG. 8A suspended by the dual axis hook assembly.

Referring now to FIGS. 7A and 7B, the hook retaining portion 26 is rotatably supported on the exterior of the tool 10 to enable the hook member 18 to be rotated or pivoted from a stowed position (FIG. 7A) to one or more extended positions (e.g., FIG. 7B) in relation to the tool housing 14. In the stowed position, the shank 22 of the hook member 18 is positioned close to the housing 14 of the tool 10 in order to minimize the possibility of the hook inadvertently contacting or catching on objects during use of the tool. As can be seen in FIGS. 1 and 2, the housing defines a hook-shaped recess 27 that is sized and shaped complementarily with respect to the hook portion 24 of the hook member 18. When the shank 22 is in the stowed position, the shank 22 can be rotated hook portion can be rotated to move the hook portion 24 to a position at which it can be located within the recess 27.

The hook retaining portion 26 of the support member 20 is configured to rotate about axis B so the hook member 18 can be moved to one or more extended positions where clearance is provided for the hook member to be rotated without obstruction about the axis A. Referring to FIG. 5, the shaft portion 28 of the support 20 is received in a bushing 46 that is supported within in a portion of the housing 14 of the tool. The bushing 46 defines a bore 48. A first end portion 50 of the bushing 46 defines a first opening 52 through which the shaft portion is introduced into the bore. A second end portion 54 of the bushing 46 defines a second opening 56 through which the end 58 of the shaft 28 protrudes.

In one embodiment, the first end portion 50 of the bushing 46 is pressed or keyed into a recess 60 provided in a first portion 62 of the housing 14. The first portion 62 of the housing 14 defines an opening 64 through which the shaft portion 28 extends prior to reaching the bushing 46. The first portion 62 of the housing also includes a planar outer surface portion 66 that provides a support surface against which the hook retaining portion 26 of the support member 20 is allowed to rotate.

The second end portion 54 of the bushing 46 is supported by a second portion 68 of the housing 14, and a fastener structure 70 (FIGS. 3A, 3B, 4A, 4B), such as a roll pin or rod, is extended through the protruding end 58 of the shaft 28 to prevent the withdrawal of the shaft 28 from the bushing 46. A detent system 70, 72 similar to the detent system used for the shank 22 of the hook member 18 may be used to provide discrete angular positioning capability for the rotatable support member 26. For example, the second end portion 54 of the bushing 46 may be provided with detent structures 72, in the form of notches or grooves, that are arrayed about the second opening 56 to the bore. The notches 72 are configured to receive the protruding portions of the roll pin 70 (FIG. 5) in the end 58 of the shaft 28.

A biasing member 74, such as a compression spring, machined spring, a spring with shape forming alloy or material, is used to bias the protruding portions of the pin 70 toward and into the notches 72 provided in the second end portion 54 of the bushing 46. In the embodiment of FIG. 5, an internal compression spring is used to provide the biasing force. As seen in FIG. 5, the shaft 28 has a stepped configuration with a larger diameter section 76 that extends from the hook retaining portion 26 through the first opening 52 in the first end portion 50 of the bushing 46. The shaft 28 transitions from the larger diameter portion 76 to a smaller diameter portion 78 within the bore 48 of the bushing 46 with the smaller diameter portion 78 extending out of the bore 48 through the second opening 56 in the second end portion 54 of the bushing 46. This transition results in a collar structure 80 being formed on the shaft 28 within the bore 48.

The first and second openings 52, 56 are sized to rotatably and translatably receive the differently sized sections 76, 78 of the shaft 28. As seen in FIG. 5, the wall that defines the bore 48 within the bushing 46 transitions from a wider diameter portion that encompasses the first opening to a narrower diameter portion that encompasses the second opening. This transition results in a ledge structure 82 being formed within the bore 48 that is arranged facing the collar structure 80 on the shaft 28. The ledge structure 82 and the collar structure 80 are spaced far enough apart from each other to provide clearance for the introduction of the compression spring 74.

In one embodiment, four evenly spaced notches 72 are provided in the second end portion 54 of the bushing 46. The notches 72 enable the hook retaining portion 26 to be retained in the stowed position (FIG. 7A) and at an extended position (FIG. 7B) that is at 90° relative to the stowed position. In alternative embodiments, more notches may be provided at smaller increments about the axis of rotation to enable the rotatable support member to be retained at multiple extended positions.

As mentioned above, one or more dual axis hook assemblies may be incorporated into the housing of a power tool at various locations depending on the type of tool, the weight distribution of the tool, the location of the handle, and other factors. In the embodiment of FIGS. 1-8, the location of the dual axis hook assembly 12 on the housing 14 of the power tool 10 is selected to provide a stable and ergonomic rest position for the tool when it is suspended. For example, referring to FIGS. 8A and 8B, the hook assembly 12 is incorporated into the upper portion of the housing 14 at a position relative to the lateral center of gravity C of the tool 10 that allows the tool to come to rest when stowed with the lateral dimension of the base plate 15 substantially horizontal. The hook assembly 12 is also located at a position relative to the front-to-rear center of gravity D of the tool 10 that allows the tool to rest when stowed in a balanced position with the tool handle 16 at an ergonomically optimized position for a user to easily grasp.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A power tool comprising:
   a housing including a motor portion and a handle portion, the motor portion enclosing a motor and drive system configured to drive a work element, the handle portion extending from the motor portion and forming a grip for placement of a user's hand, the housing having a hook assembly retaining portion in an upper portion of the housing above the handle portion; and
   a hook assembly including:
   a hook support having a hook retaining member and a shaft portion extending from the hook retaining member, the shaft portion of the hook support being rotatably retained by the hook assembly retaining portion and configured to rotate with respect to the hook assembly retaining portion of the housing about a first axis;
   a hook member having a shank portion and a hook portion, the shank portion defining a second axis and being rotatably retained by the hook retaining member of the hook support and configured to rotate with respect to the hook retaining member about the second axis, the second axis being transverse to the first axis,
   wherein the hook assembly retaining portion of the housing is configured to retain the shaft portion of the hook support at a plurality of different angular positions with respect to the first axis, and
   wherein the hook retaining member is configured to retain the shank portion of the hook member at a plurality of different angular positions with respect to the second axis,
   wherein the hook assembly retaining portion is located directly above a side-to-side center of gravity and a front-to-back center of gravity of the housing,
   wherein the hook assembly retaining portion comprises a bushing that defines a bore through which the shaft portion of the hook support extends, the bushing being retained in the upper portion of the housing,
   wherein the shaft portion of the hook support includes a transition from a first diameter section to a second diameter section within the bushing, the first diameter section having a first diameter, the second diameter section having a second diameter, the first diameter being greater than the second diameter,
   wherein the bushing defines a first opening to the bore in a first side of the bushing and a second opening to the bore on a second side of the bushing, the first opening having a size corresponding to the first diameter section, the second opening having a size corresponding to the second diameter section,
   wherein the transition of the shaft portion forms a collar structure within the bushing,
   wherein an inner wall of the bushing in which the second opening is defined forms a ledge structure that faces toward the collar structure, and
   wherein a spring is arranged on the second diameter section of the shaft portion between the collar structure and the ledge structure.

2. The power tool of claim 1, wherein the hook support is rotatable between a first position and a second position in relation to the housing,
   wherein, when the hook support is in the first position, the shank portion is oriented along an outer surface of the housing, and
   wherein, when the hook support is in the second position, the shank portion is oriented so as to extend outwardly from the housing.

3. The power tool of claim 1, wherein the hook support is configured to move axially with respect to the hook assembly retaining member between a first axial position and a second axial position,
   wherein, in the first axial position, the hook support is not allowed to rotate with respect to the hook assembly retaining member, and
   wherein, in the second axial position, the hook support is rotatable with respect to the hook assembly retaining member.

4. The power tool of claim 3, further comprising a biasing member configured to bias the hook support toward the first axial position.

5. The power tool of claim 1, wherein the shank portion is configured to move axially with respect to the hook support between a first axial position and a second axial position,
   wherein, in the first axial position, the shank support is not allowed to rotate with respect to the hook support, and
   wherein, in the second axial position, the shank portion is rotatable with respect to the hook support.

6. The power tool of claim 5, further comprising a biasing member configured to bias the shank portion toward the first axial position.

7. The power tool of claim 1, wherein the housing defines a hook-shaped recess sized and positioned to receive the hook portion of the hook member.

8. The power tool of claim 1, wherein the power tool comprises a circular saw.

* * * * *